United States Patent

Enomoto et al.

[11] Patent Number: 5,169,431
[45] Date of Patent: Dec. 8, 1992

[54] URACIL DERIVATIVES, AND THEIR PRODUCTION AND USE

[75] Inventors: Masayuki Enomoto; Susumu Takemura; Toru Uekawa, all of Hyogo; Masaharu Sakaki, Osaka, all of Japan; Ryo Sato, Durham, N.C.; Eiki Nagano, Hyogo, Japan

[73] Assignee: Sumitomo Chemical Company, Limited, Osaka, Japan

[21] Appl. No.: 763,259

[22] Filed: Sep. 20, 1991

[30] Foreign Application Priority Data

Sep. 21, 1990 [JP] Japan ............... 2-253313

[51] Int. Cl.$^5$ ............... A01N 43/48; C07D 407/04; C07D 409/04; C07D 333/56; C07D 307/87
[52] U.S. Cl. ............... 71/92; 544/310; 549/57; 549/462
[58] Field of Search ............... 544/310; 71/92; 549/57, 549/462

[56] References Cited

U.S. PATENT DOCUMENTS

| | | | |
|---|---|---|---|
| 3,740,447 | 6/1973 | Hess et al. | 548/347 |
| 3,808,335 | 4/1974 | Hess et al. | 548/347 |
| 3,920,653 | 11/1975 | Wenzelburger et al. | 71/92 |
| 4,746,352 | 5/1988 | Wenger et al. | 71/90 |
| 4,812,164 | 3/1989 | Wenger et al. | 71/92 |
| 4,859,229 | 8/1989 | Wenger et al. | 71/92 |
| 4,881,967 | 11/1989 | Semple | 71/92 |
| 4,941,909 | 7/1990 | Wenger et al. | 71/92 |
| 4,981,508 | 1/1991 | Strunk et al. | 71/92 |

FOREIGN PATENT DOCUMENTS 5641590 1/1991 Australia .
2106038 2/1971 European Pat. Off. .
0244098 4/1987 European Pat. Off. .
8902891 9/1987 European Pat. Off. .
8903825 5/1989 European Pat. Off. .
0438209 1/1990 European Pat. Off. .
0408382 7/1990 European Pat. Off. .
0420194 9/1990 European Pat. Off. .

OTHER PUBLICATIONS

Alan R. Katritzky, Handbook of Heterocyclic Chemistry, p. 460.
Chem. Abs., vol. 113, No. 10, Sep. 3, 1990.
Chem. Abs., vol., 106, No. 1, Jan. 5, 1987.

Primary Examiner—Cecilia S. Tsang
Attorney, Agent, or Firm—Birch, Stewart, Kolasch & Birch

[57] ABSTRACT

A compound of the formula:

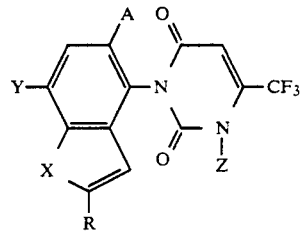

wherein R is a lower alkyl group, A is a hydrogen atom, a fluorine atom or a chlorine atom, X is an oxygen atom or a sulfur atom, Y is a hydrogen atom, a fluorine atom, a chlorine atom or a bromine atom and Z is a methyl group or an amino group, which is useful as a herbicide.

23 Claims, No Drawings

URACIL DERIVATIVES, AND THEIR PRODUCTION AND USE

The present invention relates to uracil derivatives, and their production and use. More particularly, it relates to uracil derivatives, a process for producing them, and their use as herbicides.

U.S. Pat. No. 3,920,653 discloses some uracil derivatives useful as herbicides. Also, U.S. Pat. No. 4,881,967 discloses some 2,3-dihydrobenzofurans useful as herbicides. However, these known herbicides are not sufficient in herbicidal potency or have poor selectivity between crop plants and weeds. Their herbicidal activity is thus not necessarily satisfactory.

It has now been found that uracil derivatives of the formula:

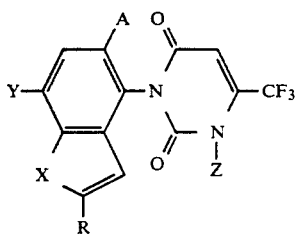
(I)

wherein R is a lower alkyl group (e.g. a $C_1$–$C_3$ alkyl group), A is a hydrogen atom, a fluorine atom or a chlorine atom, X is an oxygen atom or a sulfur atom, Y is a hydrogen atom, a fluorine atom, a chlorine atom or a bromine atom and Z is a methyl group or an amino group show a high herbicidal potency against various weeds. Thus, they produce a strong herbicidal activity against a wide variety of weeds including broad-leaved weeds, Graminaceous weeds, Commelinaceous and Cyperaceous weeds in agricultural plowed fields by foliar or soil treatment. Some of the compounds (I) do not produce any material phytotoxicity on various agricultural crops such as corn, wheat, rice plant, soybean, and cotton. Examples of the broad-leaved weeds include wild buckwheat (*Polygonum convolvulus*), pale smartweed (*Polygonum lapathifolium*), common purslane (*Portulaca oleracea*), common chickweed (*Stellaria media*), common lambsquarters (*Chenopodium album*), redroot pigweed (*Amaranthus retroflexus*), radish (*Raphanus sativus*), wild mustard (*Sinapis arvensis*), shepherdspurse (*Capsella bursa-pastoris*) hemp sesbania (*Sesbania exaltata*), sicklepod (*Cassia obtusifolia*), velvetleaf (*Abutilon theophrasti*), prickly sida (*Sida spinosa*), field pansy (*Viola arvensis*), catchweed bedstraw (*Galium aparine*), ivyleaf morningglory (*Ipomoea hederacea*), tall moringglory (*Ipomoea purpurea*), field bindweed (*Convolvulus arvensis*), purple deadnettle (*Lamium purpureum*), henbit (*Lamium amplexicaure*), jimsonweed (*Datura stramonium*), black nightshade (*Solanum nigrum*), persian speedwell (*Veronica persica*), common cocklebur (*Xanthium pensylvanicum*), common sunflower (*Helianthus annuus*), scentless chamomile (*Matricaria perforata*), corn marigold (*Chrysanthemum segetum*), sun spurge (*Euphorbia helioscopia*), spotted spurge (*Euphorbia maculata*), etc.

Examples of Graminaceous weeds include Japanese millet (*Echinochloa frumentacea*), barnyardgrass (*Echinochloa crus-galli*), green foxtail (*Setaria viridis*), large crabgrass (*Digitaria sanguinalis*), annual bluegrass (*Poa annua*), blackgrass (*Alopecurus myosuroides*), oats (*Avena sativa*), wild oats (*Avena fatua*), johnsongrass (*Sorghum halepense*), quackgrass (*Agropyron repens*), downy brome (*Bromus tectorum*), bermudagrass (*Cynodon dactylon*), giant foxtail (*Setaria faberi*), etc.

Examples of Commelinaceous weeds include asiatic dayflower (*Commelina communis*), etc. Examples of the Cyperaceous weeds include rice flatsedge (*Cyperus iria*), purple nutsedge (*Cyperus rotundus*), etc.

Some of the compounds (I) are also effective in exterminating paddy field weeds including Graminaceous weeds such as barnyardgrass (*Echinochloa oryzicola*), broad-leaved weeds such as common falsepimpernel (*Lindernia procumbens*), indian toothcup (*Rotala indica*) and waterwort (*Elatine triandra*), Cyperaceous weeds such as water nutgrass (*Cyperus serotinus*), hardstem bulrush (*Scirpus juncoides*), needle spikerush (*Eleocharis acicularis*) and umbrella sedge (*Cyperus difformis*), and others such as monochoria (*Monochoria vaginalis*) and arrowhead (*Sagittaria pygmaea*) without producing any phytotoxicity to rice plants on flooding treatment.

Among the compounds (I), preferred are those wherein X is an oxygen atom. More preferred are those wherein X is an oxygen atom and Y is a fluorine atom, a chlorine atom or a bromine atom. Especially preferred are those wherein X is an oxygen atom, Y is a fluorine atom, a chlorine atom or a bromine atom and R is a $C_1$–$C_3$ alkyl group.

Typical examples of the preferred compounds are 1-(5,7-difluoro-2-methylbenzo[b]furan-4-yl)-3-methyl-4-trifluoromethyl-1,2,3,6-tetrahydropyrimidine-2,6-dione, 1-(7-chloro-2-ethyl-5-fluorobenzo[b]furan-4-yl)-3-methyl-4-trifluoromethyl-1,2,3,6-tetrahydropyrimidine-2,6-dione, 3-amino-1-(7-chloro-2-ethyl-5-fluorobenzo[b]furan-4-yl)-4-trifluoromethyl-1,2,3,6-tetrahydropyrimidine-2,6-dione, 3-amino-1-(5,7-difluoro-2-methylbenzo[b]furan-4-yl)-4-trifluoromethyl-1,2,3,6-tetrahydropyrimidine-2,6-dione and 1-(7-chloro-5-fluoro-2-methylbenzo[b]furan-4-yl)-3-methyl-4-trifluoromethyl-1,2,3,6-tetrahydropyrimidine-2,6-dione, etc.

The compound (I) of the invention can be produced according to the following procedures.

Procedure (A):

The compound (I) can be produced by reacting a compound of the formula:

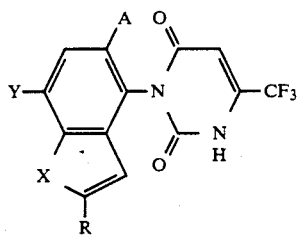
(II)

wherein R, A, X and Y are each as defined above with either one of a compound of the formula:

CH$_3$—E (III)

wherein E is a chlorine atom, a bromine atom, an iodine atom or a methanesulfonyloxy group, or a compound of the formula:

NH$_2$—G (IV)

wherein G is a methanesulfonyloxy group, a p-toluenesulfonyloxy group or a 2,4-dinitrophenoxy group.

The reaction is usually carried out in an inert solvent at a temperature of about 0° to 100° C. for a period of about 0.5 to 10 hours in the presence of a base.

The compound (III) or (IV) and the base are used respectively in amounts of about 1 to 10 equivalents and of about 1 to 1.5 equivalents to one equivalent of the compound (II). As the base, there may be used an inorganic base (e.g. sodium hydride, potassium hydride), an alkali metal alkoxide (e.g. sodium methoxide, sodium ethoxide), etc.

Examples of the inert solvent are aliphatic hydrocarbons (e.g. hexane, heptane), aromatic hydrocarbons (e.g. benzene, toluene, xylene), halogenated hydrocarbons (e.g. chloroform, carbon tetrachloride), ethers (e.g. diethyl ether, dioxane, tetrahydrofuran), ketones (e.g. acetone, methyl isobutyl ketone), esters (e.g. ethyl acetate), acid amides (e.g. N,N-dimethylformamide), sulfur compounds (e.g. dimethylsulfoxide), etc. These may be used solely or in combination.

After completion of the reaction, the reaction mixture is subjected to ordinary post-treatment. For instance, the reaction mixture is poured into water, and the precipitated crystals are collected by filtration or extracted with an organic solvent, followed by concentration. If desired, any conventional purification procedure such as chromatography or recrystallization may be applied to the resulting product.

Procedure (B):

The compound (I) of the present invention can be also produced by treating a compound of the formula:

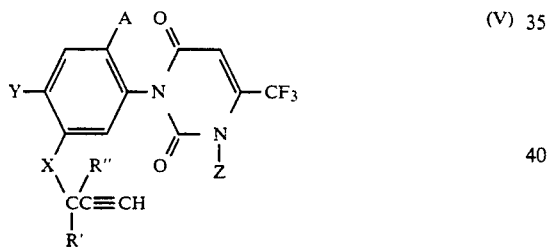

(V)

wherein R' and R" are, the same or different, each a hydrogen atom or a lower alkyl group and A, X, Y and Z are each as defined above with a base.

The reaction is usually carried out in an inert solvent at a temperature of about 20° to 200° C., preferably about 60° to 150° C. for a period of about 1 to 96 hours. As the base, there may be used an inorganic base (e.g. potassium carbonate, potassium fluoride, cesium fluoride, sodium hydride), an organic base (e.g. quaternary ammonium fluoride), an alkali metal alkoxide (e.g. sodium methoxide, sodium ethoxide), etc.

The base is used in an amount of about 0.1 to 1 equivalent to one equivalent of the compound (V). Examples of the inert solvent are aromatic hydrocarbons (e.g. toluene, xylene, mesitylene), acid amides (e.g. N,N-dimethylformamide), ethers (e.g. 1,4-dioxane, tetrahydrofuran), sulfur compounds (e.g. dimethylsulfoxide, sulphorane), etc.

After completion of the reaction, the reaction mixture is subjected to ordinary post-treatment. For instance, the reaction mixture is poured into an acidic dilution, and precipitated crystals are collected by filtration or extracted with an organic solvent, dried and concentrated. If desired, any conventional purification procedure such as recrystallization or chromatography may be applied to the resulting product.

The compound (V) can be produced by the method as disclosed in EP 260621 A or EP 408382 A.

The starting compound (II) can be produced according to the following scheme:

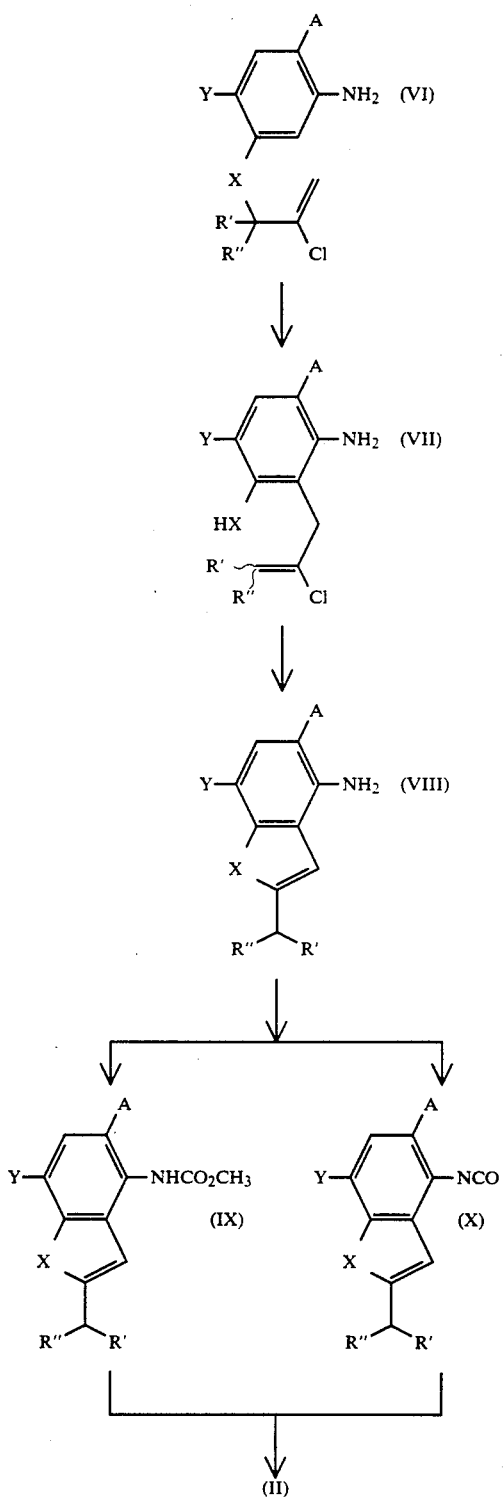

wherein R', R", A, X and Y are each as defined above.

The above reactions are explained in detail below.

Production of the compound (VII) from the compound (VI):

The compound (VII) can be produced by heating the compound (VI) in the presence or absence of an inert solvent at a temperature of about 100° to 300° C., preferably about 150° to 250° C., for a period of about 2 to 100 hours.

Examples of the inert solvent are aromatic hydrocarbons (e.g. toluene, xylene, mesitylene, tetraline), tertiary amines (e.g. N,N-diethylaniline), etc. These may be used solely or in combination.

After completion of the reaction, the reaction mixture is subjected to ordinary post-treatment. For instance, the reaction mixture is extracted with an organic solvent, followed by concentration. If desired, any conventional purification procedure such as chromatography, distillation or recrystallization may be applied to the resulting product.

The compound (VI) can be produced by the method as described in EP 61741 B from the corresponding phenol or thiophenol.

Production of the compound (VIII) from the compound (VII):

The compound (VIII) can be produced by reacting the compound (VII) in the presence of an acid.

The reaction is usually carried out in the presence or absence of an inert solvent at a temperature of about 0° to 100° C., preferably about 5° to 80° C., for a period of about 0.5 to 24 hours.

The acid is used in an amount of about 1.1 to 100 equivalents to one equivalent of the compound (VII). As the acid, there may be used inorganic acid (e.g. hydrochloric acid, sulfuric acid, polyphosphoric acid), sulfonic acid (e.g. p-toluenesulfonic acid, trifluoromethanesulfonic acid), carboxylic acid (e.g. formic acid, acetic acid, trifluoroacetic acid), etc.

Examples of the inert solvent are aromatic hydrocarbons (e.g. benzene, toluene), halogenated hydrocarbons (e.g. chloroform, carbon tetrachloride), inorganic acid (e.g. hydrochloric acid, sulfuric acid), organic acid (e.g. acetic acid) and water, etc. These may be used solely or in combination.

After completion of the reaction, the reaction mixture is subjected to ordinary post-treatment. For instance, the reaction mixture is poured into water, and precipitated crystals are collected by filtration or extracted with an organic solvent, followed by concentration. If desired, any conventional purification procedure such as chromatography, distillation or recrystallization may be applied to the resulting product.

Production of the compound (IX) from the compound (VIII):

The compound (IX) can be produced by reacting the compound (VIII) with methyl chlorocarbonate.

The reaction is usually carried out in the presence of a base in an inert solvent at a temperature of about 0° to 120° C., preferably about 20° to 80° C., for a period of about 0.5 to 5 hours. Methyl chlorocarbonate and the base are used respectively in amounts of about 1 to 2 equivalents and of about 1 to 1.5 equivalents to one equivalent of the compound (VIII). As the base, there may be used organic base (e.g. triethylamine, pyridine, N,N-diethylaniline), inorganic base (e.g. potassium carbonate, sodium hydride), etc.

Examples of the inert solvent are aromatic hydrocarbons (e.g. benzene, toluene), halogenated hydrocarbons (e.g. chloroform, carbon tetrachloride), ethers (e.g. diethyl ether, dioxane, tetrahydrofuran), ketones (e.g. acetone, methyl isobutyl ketone), acid amide (e.g. N,N-dimethylfomamide), sulfur compounds (e.g. dimethylsulfoxide), etc.

After completion of the reaction, the reaction mixture is subjected to ordinary post-treatment. For instance, the reaction mixture is poured into water and precipitated crystals are collected by filtration, or extracted with an organic solvent, followed by concentration. If desired, any conventional purification procedure such as chromatography or recrystallization may be applied to the resulting product.

Production of the compound (X) from the compound (VIII):

The compound (X) can be produced by reacting the compound (VIII) with phosgene.

The reaction is usually carried out in an inert solvent at a temperature of about 0° to 120° C., preferably about 20° to 100° C., for a period of about 0.5 to 12 hours. The phosgene is used in an amount of about 2 to 10 equivalents to one equivalent of the compound (VIII).

Examples of the inert solvent are aliphatic hydrocarbons (e.g. hexane, heptane), aromatic hydrocarbons (e.g. benzene, toluene), halogenated hydrocarbons (e.g. chloroform, carbon tetrachloride), etc. These may be used solely or in combination.

After completion of the reaction, the inert solvent and an excess phosgene are removed from the reaction mixture. If desired, any conventional purification procedure such as distillation or recrystallization may be applied to the resulting product.

Production of the compound (II) from the compound (IX):

The compound (II) is obtainable by reacting the compound (IX) with a compound of the formula:

$$CF_3(NH_2)C=CHCO_2C_2H_5 \qquad (XI)$$

in the presence of a base in an inert solvent.

The reaction is usually carried out at a temperature of about 0° to 150° C., preferably about 80° to 120° C., for a period of about 0.5 to 10 hours.

The compound (XI) and the base are used respectively in amounts of about 1 to 10 equivalents and of about 1 to 10 equivalents to one equivalent of the compound (IX). As the base, there may be used sodium hydride, potassium hydride, etc.

Examples of the inert solvent are aliphatic hydrocarbons (e.g. hexane, heptane), aromatic hydrocarbons (e.g. benzene, toluene), ethers (e.g. diethyl ether, dioxane, tetrahydrofuran), acid amides (e.g. N,N-dimethylformamide) sulfur compounds (e.g. dimethylsulfoxide), etc. These may be used solely or in combination.

After completion of the reaction, the reaction mixture is subjected to ordinary post-treatment. For example, the reaction mixture is poured into water or an acidic dilution, and precipitated crystals are collected by filtration or extracted with an organic solvent, followed by concentration. If desired, any conventional purification procedure such as chromatography, distillation or recrystallization may be applied to the resulting product.

Production of the compound (II) from the compound (X):

The compound (II) is also produced by reacting the compound (X) with the compound (XI) in the presence of a base.

The reaction is usually carried out in an inert solvent at a temperature of about 0° to 60° C., preferably about 5° to 30° C., for a period of about 0.5 to 10 hours.

The compound (XI) and the base are used respectively in amounts of about 1 to 1.5 equivalents and of about 1 to 1.5 equivalents to one equivalent of the compound (X). As the base, these may be used sodium hydride, potassium hydride, etc.

Examples of the inert solvent are aliphatic hydrocarbons (e.g. hexane, heptane), aromatic hydrocarbons (e.g. benzene, toluene), ethers (e.g. diethyl ether, dioxane, tetrahydrofuran), acid amides (e.g. N,N-dimethylformamide), sulfur compounds (e.g. dimethylsulfoxide), etc. These may be used solely or in combination.

After completion of the reaction, the reaction mixture is subjected to ordinary post-treatment. For instance, the reaction mixture is poured into water or an acidic dilution, and precipitated crystals are collected by filtration or extracted with an organic solvent, followed by concentration. If desired, any conventional purification procedure such as chromatography, distillation or recrystallization may be applied to the resulting product.

The compound (II) which is obtained by the procedures as above can be used for production of the compound (I) without further purification.

Typical embodiments for production of the compounds (I) are illustratively shown in the following Examples.

EXAMPLE 1

A mixture of ethyl 3-amino-4,4,4-trifluorocrotonate (2.1 g) and sodium hydride (0.5 g) was dissolved in N,N-dimethylformamide (0.5 g) and cooled, and a solution of 7-chloro-5-fluoro-4-methoxycarbonylamino-2-methylbenzo[b]furan (2.0 g) in N,N-dimethylformamide (5 g) was dropwise added thereto while cooling with ice. The resultant mixture was stirred for 30 minutes, followed by heating under reflux for 3 hours. After cooling, methyl iodide (0.6 g) was added thereto and the resultant mixture was allowed to stand overnight. After completion of the reaction, the reaction mixture was poured into water and extracted with ethyl acetate. The organic layer was washed with water, dried and concentrated. The residue was purified by silica gel chromatography (eluent: hexane/ethyl acetate=4/1) to give the objective compound, i.e. Compound No. 3 (1.1 g).

EXAMPLE 2

A mixture of ethyl 3-amino-4,4,4-trifluorocrotonate (1.5 g) and sodium hydride (0.2 g) was dissolved in N,N-dimethylformamide (10 ml), and a solution of 7-chloro-5-fluoro-4-methoxycarbonylamino-2-methylbenzo[b]furan (2.3 g) in N,N-dimethylformamide (10 ml) was dropwise added thereto at room temperature, followed by stirring at 120° C. for 3 hours. After cooling to room temperature, methyl iodide (2.6 g) was added thereto and the resultant mixture was stirred at room temperature for 2 hours. After completion of the reaction, the reaction mixture was poured into water and extracted with ethyl acetate. The organic layer was washed with water, dried and concentrated. The residue was purified by silica gel chromatography (eluent: hexane/ethyl acetate=4/1) to give the objective compound, i.e. Compound No. 3 (2.9 g; yeild, 86%).

$^1$H-NMR δ (ppm) (60 MHz, CDCl$_3$): 2.33 (3H, s), 3.42 (3H, s), 6.09 (1H, s), 6.20 (1H, s), 6.99 (1H, d, J=10 Hz).

EXAMPLE 3

In the same manner as in Example 2, Compound No. 2 (0.53 g; yield, 71%) was obtained by reacting 5,7-difluoro-4-methoxycarbonylamino-2-methylbenzo[b]furan (0.5 g) with ethyl 3-amino-4,4,4-trifluorocrotonate (0.35 g) and methyl iodide (0.6 g).

$^1$H-NMR δ (ppm) (60 MHz, CDCl$_3$): 2.38 (3H, s), 3.48 (3H, s), 6.14 (1H, m), 6.24 (1H, s), 7.78 (1H, t, J=10 Hz).

EXAMPLE 4

A mixture of ethyl 3-amino-4,4,4-trifluorocrotonate (0.21 g) and sodium hydride (0.03 g) was dissolved in N,N-dimethylformamide (2 ml), and a solution of 5,7-difluoro-4-methoxycarbonylamino-2-methylbenzo[b]furan (0.3 g) in N,N-dimethylformamide (2 ml) was dropwise added thereto at room temperature, followed by stirring at 120° C. for 3 hours. After cooling to room temperature, a solution of 2,4-dinitrophenoxyamine (0.3 g) in N,N-dimethylformamide (1 ml) was added thereto, and the resultant mixture was stirred at room temperature for 3 hours. After completion of the reaction, the reaction mixture was poured into water and extracted with ethyl acetate. The organic layer was washed with water, dried and concentrated. The residue was purified by silica gel chromatography (eluent: hexane/ethyl acetate=1/1) to give the objective compound, i.e. Compound No. 5 (0.06 g; yield, 13%).

$^1$H-NMR δ (ppm) (60 MHz, DMSO-d6: 2.31 (3H, s), 5.34 (2H, s), 6.19 (1H, s), 6.55 (1H, m), 7.20 (1H, t, J= 10 Hz).

EXAMPLE 5

A solution of 4-amino-7-chloro-5-fluoro-2-methylbenzo[b]thiophene (2.6 g) in toluene (10 ml) was dropwise added to a solution of phosgene (11.9 g) in toluene (20 ml) at room temperature. The resultant mixture was heated under reflux for 2 hours, followed by removal of excess phosgene to give a solution of an isocyanate derivative in toluene (20 ml). The thus obtained solution was dropwise added to a solution of ethyl 3-amino-4,4,4-trifluorocrotonate (1.6 g) and sodium hydride (0.29 g) in N,N-dimethylformamide (10 ml) at 5° C., followed by dropwise addition of methyl iodide (3.4 g) at the same temperature. The resultant mixture was further stirred at room temperature for 2 hours. After completion of the reaction, the reaction mixture was poured into water and extracted with ethyl acetate. The organic layer was washed with water, dried and concentrated. The residue was purified by silica gel chromatography (eluent: hexane/ethyl acetate=3/1) to give the objective compound, i.e. Compound No. 8 (1.7 g; yield, 36%).

$^1$H-NMR δ (ppm) (60 MHz, CDCl$_3$): 2.54 (3H, s), 3.54 (3H, s), 6.33 (1H, s), 6.67 (1H, s), 7.15 (1H, d, J=9 Hz).

EXAMPLE 6

A mixture of 1-(7-chloro-2-ethyl-5-fluorobenzo[b]furan-4-yl)-4-trifluoromethyl-1,2,3,6-tetrahydropyrimidine-2,6-dione (1.9 g) and sodium hydride (0.3 g) was dissolved in N,N-dimethylformamide (10 ml). After cooling to room temperature, methyl iodide (0.8 g) was dropwise added to the mixture, which was stirred for 30 minutes. After completion of the reaction, the reaction mixture was poured into water and extracted with ethyl acetate. The organic layer was washed with water, dried and concentrated. The residue was purified by silica gel chromatography (eluent: hexane/ethyl acetate=4/1) to give the objective compound, i.e. Compound No. 14 (0.7 g; yield, 36%).

$^1$H-NMR δ (ppm) (500 MHz, CDCl$_3$): 1.33 (3H, t, J=8 Hz), 2.75 (2H, dq, J=8 Hz(d), 1 Hz(q), 3.58 (3H, s), 6.24 (1H, t, J=1 Hz), 6.39 (1H, s), 7.15 (1H, d, J=10 Hz).

EXAMPLE 7

To a solution of 1-[4-chloro-2-fluoro-5-(1-methyl-2-propynyloxy)phenyl]-3-methyl-4-trifluoromethyl-1,2,3,6-tetrahydropyrimidine-2,6-dione (1.1 g) in mesitylene (2 ml), potassium fluoride (0.16 g) was added at room temperature, and the resultant mixture was heated under reflux for 2 hours. After cooling to room temperature, potassium fluoride was removed from the reaction mixture by filtration, followed by removal of the solvent by evaporation. The residue was purified by silica gel chromatography (eluent: hexane/ethyl acetate=4/1) to give the objective compound, i.e. Compound No. 14 (0.38 g; yield, 35%).

EXAMPLE 8

60% Sodium hydride (0.01 g) was added to dimethylformamide (20 ml), and 3-amino-1-[4-chloro-2-fluoro-5-(1-methyl-2-propynyloxy)phenyl]-4-trifluoromethyl-1,2,3,6-tetrahydropyrimidine-2,6-dione (0.71 g) was added thereto at room temperature. The resultant mixture was stirred at 100° C. for 2 days. After cooling to room temperature, the reaction mixture was poured into ice water, extracted with ethyl acetate, dried over anhydride magnesium sulfate and concentrated under reduced pressure. The residue was purified by silica gel chromatography (eluent: hexane/ethyl acetate=3/1) to give the objective compound, i.e. Compound No. 17 (0.15 g; yield, 21%).

$^1$H-NMR δ (ppm) (60 MHz, CDCl$_3$): 1.30 (3H, t, J=8 Hz), 2.79 (2H, dq, J=8 Hz(d), 1 Hz(q)), 4.58 (2H, s), 6.18 (1H, t, J=1 Hz), 6.21 (1H, s), 7.07 (1H, d, J=10 Hz).

In the same manner as above, the compounds (I) as shown in Table 1 are obtained.

TABLE 1

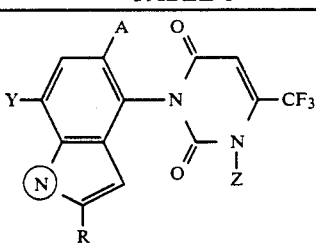

(I)

| Compound No. | R | X | Y | Z | A | Physical property |
|---|---|---|---|---|---|---|
| 1 | CH$_3$ | O | H | CH$_3$ | F | m.p., 144–145° C. |
| 2 | CH$_3$ | O | F | CH$_3$ | F | m.p., 114–115° C. |
| 3 | CH$_3$ | O | Cl | CH$_3$ | F | m.p., 105–106° C. |
| 4 | CH$_3$ | O | Br | CH$_3$ | F | m.p., 154–156° C. |
| 5 | CH$_3$ | O | F | NH$_2$ | F | m.p., 195–197° C. |
| 6 | CH$_3$ | O | Cl | NH$_2$ | F | |
| 7 | CH$_3$ | S | F | CH$_3$ | F | |
| 8 | CH$_3$ | S | Cl | CH$_3$ | F | m.p., 160–161° C. |
| 9 | CH$_3$ | S | Br | CH$_3$ | F | |
| 10 | CH$_3$ | S | F | NH$_2$ | F | |

TABLE 1-continued

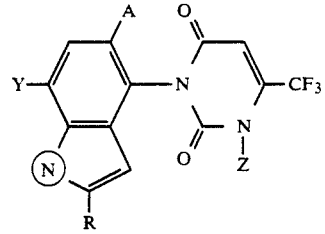

(I)

| Compound No. | R | X | Y | Z | A | Physical property |
|---|---|---|---|---|---|---|
| 11 | CH$_3$ | S | Cl | NH$_2$ | F | - |
| 12 | C$_2$H$_5$ | O | H | CH$_3$ | F | |
| 13 | C$_2$H$_5$ | O | F | CH$_3$ | F | |
| 14 | C$_2$H$_5$ | O | Cl | CH$_3$ | F | m.p., 135–136° C. |
| 15 | C$_2$H$_5$ | O | Br | CH$_3$ | F | |
| 16 | C$_2$H$_5$ | O | F | NH$_2$ | F | |
| 17 | C$_2$H$_5$ | O | Cl | NH$_2$ | F | m.p., 166–167° C. |
| 18 | C$_2$H$_5$ | S | F | CH$_3$ | F | |
| 19 | C$_2$H$_5$ | S | Cl | CH$_3$ | F | |
| 20 | C$_2$H$_5$ | S | Br | CH$_3$ | F | |
| 21 | C$_2$H$_5$ | S | F | NH$_2$ | F | |
| 22 | C$_2$H$_5$ | S | Cl | NH$_2$ | F | |
| 23 | CH$_3$ | O | H | CH$_3$ | H | |
| 24 | CH$_3$ | O | F | CH$_3$ | H | |
| 25 | CH$_3$ | O | Cl | CH$_3$ | H | m.p., 139–141° C. |
| 26 | CH$_3$ | O | Br | CH$_3$ | H | |
| 27 | CH$_3$ | O | F | NH$_2$ | H | |
| 28 | CH$_3$ | O | Cl | NH$_2$ | H | |
| 29 | CH$_3$ | S | H | CH$_3$ | H | |
| 30 | CH$_3$ | S | F | CH$_3$ | H | |
| 31 | CH$_3$ | S | Cl | CH$_3$ | H | |
| 32 | CH$_3$ | S | Br | CH$_3$ | H | |
| 33 | CH$_3$ | S | F | NH$_2$ | H | |
| 34 | CH$_3$ | S | Cl | NH$_2$ | H | |
| 35 | C$_2$H$_5$ | O | H | CH$_3$ | H | |
| 36 | C$_2$H$_5$ | O | F | CH$_3$ | H | |
| 37 | C$_2$H$_5$ | O | Cl | CH$_3$ | H | |
| 38 | C$_2$H$_5$ | O | Br | CH$_3$ | H | |
| 39 | C$_2$H$_5$ | O | F | NH$_2$ | H | |
| 40 | C$_2$H$_5$ | O | Cl | NH$_2$ | H | |
| 41 | C$_2$H$_5$ | S | H | CH$_3$ | H | |
| 42 | C$_2$H$_5$ | S | F | CH$_3$ | H | |
| 43 | C$_2$H$_5$ | S | Cl | CH$_3$ | H | |
| 44 | C$_2$H$_5$ | S | Br | CH$_3$ | H | |
| 45 | C$_2$H$_5$ | S | F | NH$_2$ | H | |
| 46 | C$_2$H$_5$ | S | Cl | NH$_2$ | H | |
| 47 | CH$_3$ | O | H | CH$_3$ | Cl | |
| 48 | CH$_3$ | O | F | CH$_3$ | Cl | |
| 49 | CH$_3$ | O | Cl | CH$_3$ | Cl | m.p., 125–127° C. |
| 50 | CH$_3$ | O | Br | CH$_3$ | Cl | |
| 51 | CH$_3$ | O | F | NH$_2$ | Cl | |
| 52 | CH$_3$ | O | Cl | NH$_2$ | Cl | |
| 53 | CH$_3$ | S | H | CH$_3$ | Cl | |
| 54 | CH$_3$ | S | F | CH$_3$ | Cl | |
| 55 | CH$_3$ | S | Cl | CH$_3$ | Cl | |
| 56 | CH$_3$ | S | Br | CH$_3$ | Cl | |
| 57 | CH$_3$ | S | F | NH$_2$ | Cl | |
| 58 | CH$_3$ | S | Cl | NH$_2$ | Cl | |
| 59 | C$_2$H$_5$ | O | H | CH$_3$ | Cl | |
| 60 | C$_2$H$_5$ | O | F | CH$_3$ | Cl | |
| 61 | C$_2$H$_5$ | O | Cl | CH$_3$ | Cl | |
| 62 | C$_2$H$_5$ | O | Br | CH$_3$ | Cl | |
| 63 | C$_2$H$_5$ | O | F | NH$_2$ | Cl | |
| 64 | C$_2$H$_5$ | O | Cl | NH$_2$ | Cl | |
| 65 | C$_2$H$_5$ | S | H | CH$_3$ | Cl | |
| 66 | C$_2$H$_5$ | S | F | CH$_3$ | Cl | |
| 67 | C$_2$H$_5$ | S | Cl | CH$_3$ | Cl | |
| 68 | C$_2$H$_5$ | S | Br | CH$_3$ | Cl | |
| 69 | C$_2$H$_5$ | S | F | NH$_2$ | Cl | |
| 70 | C$_2$H$_5$ | S | Cl | NH$_2$ | Cl | |
| 71 | n-C$_3$H$_7$ | O | F | CH$_3$ | F | |
| 72 | n-C$_3$H$_7$ | O | F | NH$_2$ | F | |
| 73 | n-C$_3$H$_7$ | O | Cl | CH$_3$ | F | |
| 74 | n-C$_3$H$_7$ | O | Cl | CH$_3$ | Cl | |

Typical embodiments for preparation of the starting compounds (VII), (VIII) and (IX) are illustratively shown in the following examples.

EXAMPLE 9

Compound (VII)

A mixture of 2-chloro-4-fluoro-5-nitrophenol (20.3 g) and 2,3-dichloropropene (11.7 g) was dissolved in N,N-dimethylformamide (200 ml), and potassium carbonate (14.6 g) was added thereto at room temperature, and the resultant mixture was stirred at 80° C. for 2 hours. After cooling to room temperature, the reaction mixture was poured into water and extracted with ethyl acetate. The organic layer was washed with water, dried and concentrated. The residue was purified by silica gel chromatography (eluent: hexane/ethyl acetate=4/1) to give 4-chloro-5-(2-chloro-2-propenyloxy)2-fluoronitrobenzene (14.8 g; yield, 53%).

$^1$H-NMR δ (ppm) (60 MHz, CDCl$_3$): 4.55 (2H, s), 5.38 (1H, br), 5.51 (1H, br), 7.21 (1H, d, J=10 Hz), 7.45 (1H, d, J=6 Hz).

A solution of 4-chloro-5-(2-chloro-2-propenyloxy)-2-fluoronitrobenzene (12.8 g) thus obtained in ethyl acetate (50 ml) was dropwise added to a suspension of iron powder (13.4 g) in acetic acid (200 ml) and water (20 ml) at 80° C. for 10 minutes while stirring vigorously. Stirring was continued at 80° C. for 0.5 hour, and the reaction mixture was cooled to 60° C., followed by addition of ethyl acetate (500 ml). Insoluble materials were removed by filtration, and the filtrate was washed with a 5% NaHCO$_3$ solution to remove acetic acid, dried and concentrated to give 4-chloro-5-(2-chloro-2-propenyloxy)-2-fluoroaniline (11.5 g).

$^1$H-NMR δ (ppm) (60 MHz, CDCl$_3$): 3.6–3.9 (2H, br), 4.51 (2H, s), 5.41 (1H, br), 5.60 (1H, br), 6.33 (1H, d, J=8 Hz), 6.98 (1H, d, J=10 Hz).

A solution of 4-chloro-5-(2-chloro-2-propenyloxy)-2-fluoroaniline (10.4 g) thus obtained in N,N-diethylaniline (20 ml) was heated under reflux for 12 hours. After cooling to room temperature, the reaction mixture was dissolved in ethyl acetate and washed with 10% hydrochloric acid three times. After removal of N,N-diethylaniline, the reaction mixture was dried and concentrated. The residue was purified by silica gel chromatography (eluent: hexane/ethyl acetate=4/1) to give 3-amino-6-chloro-2-(2-chloro-2-propenyl)-4-fluorophenol (7.4 g; yield, 71%). m.p., 50.5°–51.5° C.

$^1$H-NMR δ (ppm) (60 MHz, CDCl$_3$): 3.67 (2H, s), 3.6–3.9 (2H, br), 5.05 (1H, br), 5.20 (1H, br), 5.43 (1H, s), 6.89 (1H, d, J=10 Hz).

EXAMPLE 10

Compound (VIII)

3-Amino-6-chloro-2-(2-chloro-2-propenyl)-4-fluorophenol (4.8 g) was dissolved in chloroform (20 ml), and trifluoromethanesulfonic acid (4.6 g) was dropwise added thereto at 5° C. for 5 minutes, followed by stirring at room temperature for 5 hours. After completion of the reaction, the reaction mixture was poured into a 5% NaOH solution (30 ml) at 5° C. and extracted with ethyl acetate. The organic layer was dried and concentrated to give 4-amino-7-chloro-5-fluoro-2-methylbenzo[b]furan (3.5 g; yield, 86%).

EXAMPLE 11

COMPOUND (VIII)

A mixture of 5-amino-2-chloro-4-fluorothiophenol (8.89 g) and anhydride potassium carbonate (3.5 g) was dissolved in N,N-dimethylformamide (100 ml), and 2,3-dichloropropene (6.65 g) was added thereto. The resultant mixture was stirred at 20° to 40° C. for 4 hours. After completion of the reaction, the reaction mixture was extracted with ether, washed with water, dried and concentrated. The residue was purified by silica gel chromatography (eluent: hexane/ethyl acetate=7/1) to give 4-chloro-2-fluoro-5-(2-chloro-2-propenylthio)aniline (10.5 g; yield, 84%).

A solution of 4-chloro-2-fluoro-5-(2-chloro-2-propenyloxythio)aniline (10.0 g) thus obtained in N,N-diethylaniline (25 ml) was heated under reflux for 6 hours. After cooling to room temperature, the reaction mixture was made acidic (pH 2) with addition of 10% hydrochloric acid and stirred at room temperature for 1 hour. The reaction mixture was extracted with ethyl acetate, washed with water, dried and concentrated. The residue was crystallized and washed with a mixture of hexane and ether to give 4-amino-7-chloro-5-fluoro-2-methylbenzo[b]thiophene (3.4 g).

In the same manner as in Examples 10 and 11, the compounds (VIII) as shown in Table 2 were obtained.

TABLE 2

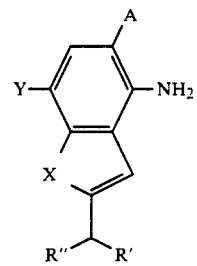

(VIII)

| R' | R" | X | Y | A | Physical property |
|---|---|---|---|---|---|
| H | H | O | Cl | F | m.p., 107.5–109° C. $^1$H-NMR δ (ppm) (60 MHz, CDCl$_3$): 2.31 (3H, d, J = 1 Hz), 3.7–4.0 (2H, br), 6.19 (1H, q, J = 1 Hz), 6.88 (1H, d, J = 10 Hz). |
| H | H | O | H | F | $^1$H-NMR δ (ppm) (90 MHz, CDCl$_3$): 2.40 (3H, d, J = 2 Hz), 3.5–3.9 (2H, br), 6.24 (1H, q, J = 2 Hz), 6.69 (1H, dd, J = 4 Hz (d), 8 Hz (d)), 6.88 (1H, t, J = 8 Hz). |
| H | H | O | F | F | m.p., 53.5–54.5° C. $^1$H-NMR δ (ppm) (60 MHz, CDCl$_3$): 2.43 (3H, d, J = 1 Hz), 3.8–4.0 (2H, br), 6.2–6.3 (1H, br), 6.68 (1H, t, J = 11 Hz). |
| H | H | O | Br | F | m.p., 109.5–112° C. $^1$H-NMR δ (ppm) (60 MHz, CDCl$_3$): 2.36 (3H, d, J = 1 Hz), 3.5–3.8 (2H, br), 6.12 (1H, q, J = 1 Hz), 6.80 (1H, d, J = 10 Hz). |
| H | H | O | Cl | H | m.p., 95–96° C. $^1$H-NMR δ (ppm) (60 MHz, CDCl$_3$): 2.32 (3H, s), 3.5–3.8 (2H, br), 6.14 (1H, s), 6.21 (1H, d, J = 8 Hz), 6.83 (1H, d, J = 8 Hz) |
| H | H | O | Cl | Cl | m.p., 105.5–106.5° C. $^1$H-NMR δ (ppm) (60 MHz, CDCl$_3$): 2.35 (3H, s), 3.9–4.1 (2H, br), 6.14 (1H, s), 6.95 (1H, s) |
| H | H | S | Cl | F | m.p., 127–128° C. $^1$H-NMR δ (ppm) (60 MHz, CDCl$_3$): 2.54 (3H, s), 3.7–4.0 (2H, br), 6.82 (1H, s), 6.95 (1H, d, J = 10 |

TABLE 2-continued

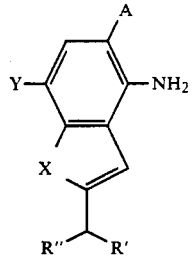
(VIII)

| R' | R" | X | Y | A | Physical property |
|---|---|---|---|---|---|
| | | | | | Hz). |

EXAMPLE 12

COMPOUND (IX)

A mixture of 4-amino-7-chloro-5-fluoro-2-methylbenzo[b]furan (3.4 g) and N,N-diethylaniline (2.6 g) was dissolved in tetrahydrofuran (20 ml), and methyl chlorocarbonate (1.6 g) was dropwise added thereto at room temperature. The resultant mixture was heated under reflux for 3 hours. After cooling to room temperature, the reaction mixture was dissolved in ethyl acetate and washed with 10% hydrochloric acid. After removal of N,N-diethylaniline, the reaction mixture was dried and concentrated. The residue was washed with hexane to give 7-chloro-5-fluoro-4-methoxycarbonylamino-2-methylbenzo[b]furan (3.8 g; yield, 87%). m.p., 168°-169° C.

$^1$H-NMR $\delta$ (ppm) (60 MHz, CDCl$_3$): 2.30 (3H, s), 3.71 (3H, s), 6.20 (1H, br), 6.30 (1H, s), 7.09 (1H, d, J=10 Hz).

EXAMPLE 13

COMPOUND (IX)

In the same manner as in Example 12, 5,7-difluoro-4-methoxycarbonylamino-2-methylbenzo[b]furan was obtained by reacting 4-amino-5,7-difluoro-2-methylbenzo[b]furan with methyl chlorocarbonate. m.p., 156°-158° C.

$^1$H-NMR $\delta$ (ppm) (60 MHz, DMSO-d6): 2.26 (3H, s), 3.45 (3H, s), 6.39 (1H, br), 7.00 (1H, t, J=11 Hz), 9.05 (1H, br).

For the practical usage of the compound (I), it is usually formulated with conventional solid or liquid carriers or diluents as well as surface active agents or auxiliary agents into conventional preparation forms such as emulsifiable concentrates, wettable powders, flowables, water dispersible granules and granules. The content of the compound (I) as the active ingredient in such preparation forms is normally within a range of about 0.005 to 80% by weight, preferably of about 0.01 to 70% by weight. Examples of the solid carrier or diluent are fine powders or granules of kaolin clay, attapulgite clay, bentonite, terra alba, pyrophyllite, talc, diatomaceous earth, calcite, walnut shell powders, urea, ammonium sulfate and synthetic hydrous silicate, etc. As the liquid carrier or diluent, there may be exemplified aromatic hydrocarbons (e.g. xylene, methylnaphthalene), alcohols (e.g. isopropanol, ethylene glycol, cellosolve), ketones (e.g. acetone, cyclohexanone, isophorone), soybean oil, cotton seed oil, dimethylsulfoxide, N,N-dimethylformamide, acetonitrile, water, etc.

The surface active agent used for emulsification, dispersing or spreading may be of any type, for instance, either anionic or non-ionic. Examples of the surface active agent include alkylsulfates, alkylsulfonates, alkylarylsulfonates, dialkylsulfosuccinates, phosphates of polyoxyethylenealkylaryl ethers, polyoxyethylene alkyl ethers, polyoxyethylene alkylaryl ethers, polyoxyethylene polyoxypropylene block copolymer, sorbitan fatty acid esters, polyoxyethylene sorbitan fatty acid esters, etc. Examples of the auxiliary agents include ligninsulfonates, sodium alginate, polyvinyl alcohol, gum arabic, CMC (carboxymethyl cellulose), PAP (isopropyl acid phosphate), etc.

Practical embodiments of the herbicidal composition according to the present invention are illustratively shown in the following examples wherein parts are by weight. The number of the active ingredient corresponds to the one in Table 1.

FORMULATION EXAMPLE 1

Fifty parts of any one of Compound Nos. 1 to 5, 8, 14, 17, 25 and 49, 3 parts of calcium ligninsulfonate, 2 parts of sodium laurylsulfate and 45 parts of synthetic hydrous silicate are well mixed while being powdered to obtain a wettable powder.

FORMULATION EXAMPLE 2

Five parts of any one of Compound Nos. 1 to 5, 8, 14, 17, 25 and 49, 14 parts of polyoxyethylenestyrylphenyl ether, 6 parts of calcium dodecylbenzenesulfonate, 25 parts of xylene and 50 parts of cyclohexanone are well mixed to obtain an emulsifiable concentrate.

FORMULATION EXAMPLE 3

Two parts of any one of Compound Nos. 1 to 5, 8, 14, 17, 25 and 49, 1 part of synthetic hydrous silicate, 2 parts of calcium ligninsulfonate, 30 parts of bentonite and 65 parts of kaolin clay are well mixed while being powdered. The mixture is then kneaded with water, granulated and dried to obtain granules.

FORMULATION EXAMPLE 4

Twenty-five parts of any one of Compound Nos. 1 to 5, 8, 14, 17, 25 and 49 are mixed with 3 parts of polyoxyethylene sorbitan monooleate, 3 parts of carboxymethyl cellulose and 69 parts of water and pulverized until the particle size of the mixture becomes less than 5 microns to obtain a flowable.

FORMULATION EXAMPLE 5

0.05 part of any one of Compound Nos. 1 to 5, 8, 14, 17, 25 and 49, 1 part of synthetic hydrous silicate, 2 parts of calcium ligninsulfonate, 30 parts of bentonite and 66.95 parts of kaolin clay are well mixed while being powdered. The mixture is then kneaded with water, granulated and dried to obtain granules.

The compound (I) thus formulated in any suitable preparation form is useful for pre-emergence or post-emergence control of undesired weeds by soil or foliar treatment as well as flood fallowing treatment. These treatments include application to the soil surface prior to or after planting, incorporation into the soil prior to planting or transplanting, etc. The foliar treatment may be effected by spraying the herbicidal composition containing the compound (I) over the top of plants. It may also be applied directly to the weeds if care is taken to keep the chemical off the crop foliage.

The compound (I) may be used together with any other herbicide to improve its activity as a herbicide.

Further, it may be applied in combination with an insecticide, an acaricide, a nematocide, a fungicide, a plant growth regulator, a fertilizer, a soil improver, etc. It is also useful as a herbicide to be employed for orchards, pasture lands, lawns, forests, non-agricultural fields, etc.

The dosage of the compound (I) may vary depending on the prevailing weather conditions, the formulation used, the prevailing season, the mode of application, the soil involved, the crop and weed species, etc. Generally, however, the dosage is from about 0.005 to 80 grams, preferably from about 0.02 to 40 grams, of the active ingredient per are. The herbicidal composition of the invention formulated in the form of an emulsifiable concentrate, a wettable powder, a water-dispersible granule or a flowable may ordinarily be employed by diluting it with water at a volume of about 1 to 10 liters per are, if necessary, with addition of an auxiliary agent such as a spreading agent. Examples of the spreading agent include, in addition to the surface active agents as noted above, polyoxyethylene resin acid (ester), ligninsulfonate, abietic acid salt, dinaphthylmethanedisulfonate, paraffin, etc. The composition formulated in the form of granules may be normally applied as such without dilution.

The biological data of the compound (I) as herbicides will be illustratively shown in the following Examples wherein the phytotoxicity to crop plants and the herbicidal activity on weeds were observed visually as to the degree of germination as well as the growth inhibition and rated with an index 0, 1, 2, 3, 4 or 5, the numeral "0" indicating no material difference as seen in comparison with the untreated plants and the numeral "5" indicating the complete inhibition or death of the test plants.

The compounds as shown in Table 3 were used for comparison.

TABLE 3

| Compound No. | Structure | Remarks |
|---|---|---|
| A | 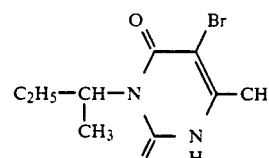 | Bromacil |
| B | 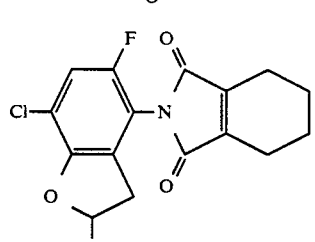 | U.S. Pat. No. 4,881,967 |
| C | 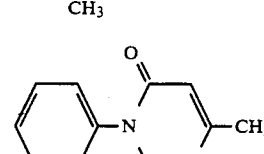 | U.S. Pat. No. 3,920,653 |

TEST EXAMPLE 1

Cylindrical plastic pots (diameter, 10 cm; height, 10 cm) were filled with upland field soil, and the seeds of Japanese millet, tall morningglory and velvetleaf were sowed therein and covered with soil. A designated amount of the test compound formulated in an emulsifiable concentrate as in Formulation Example 2 was diluted with water, and the dilution was sprayed onto the soil surface by means of a small hand sprayer at a spray volume of 10 liters per are. The test plants were grown in a greenhouse for 20 days, and the herbicidal activity was examined. The results are shown in Table 4.

TABLE 4

| | | Herbicidal activity | | |
|---|---|---|---|---|
| Compound No. | Dosage (g/are) | Japanese millet | Tall morning-glory | Velvet-leaf |
| 1 | 5 | 5 | 5 | 5 |
| 2 | 5 | 5 | 5 | 5 |
| 3 | 5 | | | |
| 4 | 5 | 5 | 5 | 5 |
| 5 | 5 | 5 | 5 | 5 |
| 8 | 5 | 5 | 5 | 5 |
| 14 | 5 | 5 | 5 | 5 |
| 17 | 5 | 5 | 5 | 5 |
| C | 5 | 0 | 0 | 0 |

TEST EXAMPLE 2

Cylindrical plastic pots (diameter, 10 cm; height, 10 cm) were filled with upland field soil, and the seeds of Japanese millet, tall morningglory, radish and velvetleaf were sowed therein and cultivated in a greenhouse for 10 days. A designated amount of the test compound formulated in an emulsifiable concentrate as in Formulation Example 2 was diluted with water containing a spreading agent, and the dilution was sprayed over the foliage of the test plant by means of a small hand sprayer at a spray volume of 10 liters per are. The test plants were further grown in the greenhouse for 20 days, and the herbicidal activity was examined. The results are shown in Table 5.

TABLE 5

| | | Herbicidal activity | | | |
|---|---|---|---|---|---|
| Compound No. | Dosage (g/are) | Japanese millet | Tall morning-glory | Radish | Velvet-leaf |
| 2 | 0.63 | 5 | 5 | 5 | 5 |
| 3 | 0.63 | 5 | 5 | 5 | 5 |
| 4 | 0.63 | 4 | 5 | 5 | 5 |
| 5 | 0.63 | 3 | 5 | 5 | 5 |
| 8 | 0.63 | 5 | 5 | 5 | 5 |
| 14 | 0.63 | 5 | 5 | 5 | 5 |
| 17 | 0.63 | 5 | 5 | 5 | 5 |
| C | 0.63 | 0 | 0 | 0 | 0 |

TEST EXAMPLE 3

Cylindrical plastic pots (diameter, 8 cm; height, 12 cm) were filled with paddy field soil, and the seeds of barnyardgrass, broad-leaved weeds (common falsepimpernel, indian toothcup, warterwort) were sowed therein in 1 to 2 cm depth. After flooding, rice seedlings of 2-leaf stage were transplanted and cultivated in a greenhouse for 6 days. A designated amount of the test compound formulated in an emulsifiable concentrate as in Formulation Example 2 was diluted with water (5 ml), and applied onto water surface. The test plants were further grown in the greenhouse for 20 days, and the herbicidal activity and phytotoxicity were examined. At the time of the treatment, weeds were in general about to germ. The results are shown in Table 6.

TABLE 6

| Compound No. | Dosage (g/are) | Phytotoxicity Rice plant | Herbicidal activity Barnyardgrass | Herbicidal activity Broad-leaved weeds |
|---|---|---|---|---|
| 3 | 0.04 | 0 | 5 | 5 |
| 4 | 0.16 | 0 | 5 | 5 |
| 8 | 0.16 | 1 | 5 | 5 |
| 14 | 0.04 | 1 | 5 | 5 |
| 17 | 0.16 | 0 | 5 | 5 |
| C | 0.04 | 0 | 0 | 0 |

TEST EXAMPLE 4

Vats (33 cm × 23 cm × 11 cm) were filled with upland field soil, and the seeds of cotton, corn, black nightshade, velvetleaf, tall morningglory and giant foxtail were sowed therein in 1 to 2 cm depth. A designated amount of the test compound formulated in an emulsifiable concentrate as in Formulation Example 2 was diluted with water, and the dilution was sprayed onto the soil surface by means of a small hand sprayer at a spray volume of 10 liters per are. The test plants were grown in a greenhouse for 20 days, and the herbicidal activity and the phytotoxicity were examined. The results are shown in Table 7.

TABLE 7

| Compound No. | Dosage (g/are) | Phytotoxicity Cotton | Phytotoxicity Corn | Herbicidal activity Black nightshade | Herbicidal activity Velvetleaf | Herbicidal activity Tall morningglory | Herbicidal activity Giant foxtail |
|---|---|---|---|---|---|---|---|
| 2 | 0.08 | 1 | 1 | 5 | 5 | 4 | — |
| 3 | 1.25 | — | 1 | 5 | 5 | 5 | 5 |
|  | 0.31 | 1 | 0 | 5 | 5 | — | 5 |
| 8 | 1.25 | 1 | — | 5 | 5 | 5 | 5 |
| 14 | 1.25 | 1 | — | 5 | 5 | 5 | 5 |
|  | 0.31 | 0 | 1 | 5 | 5 | 4 | 5 |
| B | 1.25 | 2 | 0 | 0 | 1 | 0 | 3 |
|  | 0.31 | 0 | 0 | 0 | 0 | 0 | 2 |

TEST EXAMPLE 5

Vats (33 cm × 23 cm × 11 cm) were filled with upland field soil, and the seeds of soybean, rice plant, black nightshade and velvetleaf were sowed therein in 1 to 2 cm depth. A designated amount of the test compound formulated in an emulsifiable concentrate as in Formulation Example 2 was diluted with water, and the dilution was sprayed onto the soil surface by means of a small hand sprayer at a spray volume of 10 liters per are. The test plants were grown in a greenhouse for 20 days, and the herbicidal activity and the phytotoxicity were examined. The results are shown in Table 8.

TABLE 8

| Compound No. | Dosage (g/are) | Phytotoxicity Soybean | Herbicidal activity Rice plant | Herbicidal activity Black nightshade | Herbicidal activity Velvetleaf |
|---|---|---|---|---|---|
| 1 | 0.08 | 0 | 1 | 4 | 5 |
| 2 | 0.02 | 0 | 1 | 5 | 4 |
| 3 | 0.08 | — | 0 | 5 | 4 |
| 14 | 0.08 | 0 | 1 | 5 | 4 |
| B | 0.08 | 0 | 0 | 0 | 0 |

TEST EXAMPLE 6

Vats (33 cm × 23 cm × 11 cm) were filled with upland field soil, and the seeds of cotton, prickly sida, sun spurge, velvetleaf and giant foxtail were sowed therein in 1 to 2 cm depth. A designated amount of the test compound formulated in an emulsifiable concentrate as in Formulation Example 2 was diluted with water, and the dilution was sprayed onto the soil surface by means of a small hand sprayer at a spray volume of 10 liters per are. The test plants were grown in a greenhouse for 20 days, and the herbicidal activity and the phytotoxicity were examined. The results are shown in Table 9.

TABLE 9

| Compound No. | Dosage (g/are) | Phytotoxicity Cotton | Herbicidal activity Prickly sida | Herbicidal activity Sun spurge | Herbicidal activity Velvetleaf | Herbicidal activity Giant foxtail |
|---|---|---|---|---|---|---|
| 14 | 0.63 | 0 | 5 | 5 | 5 | 5 |
|  | 0.16 | 0 | 5 | 5 | 5 | 5 |

TEST EXAMPLE 7

Vats (33 cm × 23 cm × 11 cm) were filled with upland field soil, and the seeds of wheat, pale smartweed, common chickweed, field pansy, persian speedwell and annual bluegrass were sowed therein in 1 to 2 cm depth. A designated amount of the test compound formulated in an emulsifiable concentrate as in Formulation Example 2 was diluted with water, and the dilution was sprayed onto the soil surface by means of a small hand sprayer at a spray volume of 10 liters per are. The test plants were grown in a greenhouse for 27 days, and the herbicidal activity and the phytotoxicity were examined. The results are shown in Table 10.

TABLE 10

| Compound No. | Dosage (g/are) | Phytotoxicity Wheat | Herbicidal activity Pale smartweed | Herbicidal activity Common chickweed | Herbicidal activity Field pansy | Herbicidal activity Persian speedwell | Herbicidal activity Annual bluegrass |
|---|---|---|---|---|---|---|---|
| 3 | 1.25 | — | 5 | 5 | 5 | 5 | 5 |
|  | 0.31 | 1 | 5 | — | 5 | 5 | 4 |
| 8 | 1.25 | 0 | 5 | — | 5 | 5 | 4 |
| 14 | 1.25 | 1 | 5 | 5 | 5 | 5 | 5 |
|  | 0.31 | 0 | 5 | 5 | 5 | 5 | 4 |
| 17 | 0.31 | 1 | 5 | 5 | 5 | 5 | 4 |

TEST EXAMPLE 8

Vats (33 cm × 23 cm × 11 cm) were filled with upland field soil, and the seeds of barnyardgrass, common cocklebur, tall morningglory, black nightshade and velvetleaf were sowed therein and cultivated in a greenhouse for 18 days. A designated amount of the test compound formulated in an emulsifiable concentrate as in Formulation Example 2 was diluted with water containing a spreading agent, and the dilution was sprayed over the foliage of the test plant by means of a small hand sprayer at a spray volume of 10 liters per are. The test plants were further grown in the greenhouse for 20 days, and the herbicidal activity was examined. At the time of the application, the test plants were generally at the 1 to 4 leaf stage and in 6 to 30 cm height, although the growing stage of the test plants varied depending on their species. The results are shown in Table 11.

TABLE 11

| Compound No. | Dosage (g/are) | Herbicidal activity | | | | |
|---|---|---|---|---|---|---|
| | | Barn-yard-grass | Common cock-lebur | Tall morning-glory | Black night-shade | Velvet-leaf |
| 2 | 0.08 | 4 | 5 | 5 | 5 | 5 |
| 3 | 0.08 | 4 | 5 | 5 | 5 | 5 |
| | 0.02 | 4 | — | 4 | 5 | 5 |
| 14 | 0.08 | 5 | 5 | 5 | 5 | 5 |
| | 0.02 | 5 | 5 | 5 | 5 | 5 |
| A | 0.08 | 0 | 0 | 0 | 3 | 2 |
| | 0.02 | 0 | 0 | 0 | 2 | 1 |
| B | 0.08 | 4 | 2 | 2 | 5 | 4 |
| | 0.02 | 3 | 2 | 2 | 5 | 3 |

TEST EXAMPLE 9

Vats (33 cm × 23 cm × 11 cm) were filled with upland field soil, and the seeds of pale smartweed, field pansy, persian speedwell and catchweed bedstraw were sowed therein in 1 to 2 cm depth, and cultivated in a greenhouse for 31 days. A designated amount of the test compound formulated in an emulsifiable concentrate as in Formulation Example 2 was diluted with water containing a spreading agent, and the dilution was sprayed over the foliage of the test plants by means of a small hand sprayer at a spray volume of 10 liters per are. The test plants were further grown in the greenhouse for 27 days, and the herbicidal activity was examined. At the time of the application, the test plants were generally at 1 to 4 leaf stage and in 2 to 12 cm height, although the growing stage of the test plants varied depending on their species. The results are shown in Table 12.

TABLE 12

| Compound No. | Dosage (g/are) | Herbicidal activity | | | |
|---|---|---|---|---|---|
| | | Pale smart-weed | Field pansy | Persian speed-well | Catchweed bedstraw |
| 3 | 0.31 | 5 | 4 | 4 | 5 |
| | 0.08 | 5 | 4 | — | 5 |
| 14 | 0.31 | 5 | 5 | 5 | 5 |
| | 0.08 | 5 | 5 | 4 | 5 |
| A | 0.31 | 2 | 0 | 0 | 2 |
| | 0.08 | 0 | 0 | 0 | 0 |
| B | 0.31 | 2 | 2 | 1 | 2 |
| | 0.08 | 2 | 2 | 1 | 1 |

What is claimed is:

1. A compound of the formula:

[Chemical structure with substituents A, Y, X, R on a benzofuran ring attached to a tetrahydropyrimidine-2,6-dione ring bearing CF$_3$ and N-Z groups]

wherein R is a lower alkyl group, A is a hydrogen atom, a fluorine atom or a chlorine atom, X is an oxygen atom or a sulfur atom, Y is a hydrogen atom, a fluorine atom, a chlorine atom or a bromine atom and Z is a methyl group or an amino group.

2. The compound according to claim 1, wherein X is an oxygen atom.

3. The compound according to claim 1, wherein X is an oxygen atom and Y is a fluorine atom, a chlorine atom or a bromine atom.

4. The compound according to claim 1, wherein X is an oxygen atom, Y is a fluorine atom, a chlorine atom or a bromine atom and R is a C$_1$-C$_3$ alkyl group.

5. The compound according to claim 1, wherein R is a methyl or an ethyl group and A is a fluorine atom.

6. The compound according to claim 5, wherein X is an oxygen atom.

7. The compound according to claim 5, wherein R is a methyl group.

8. The compound according to claim 1, which is 1-(5,7-difluoro-2-methylbenzo[b]furan-4-yl)-3-methyl-4-trifluoromethyl-1,2,3,6-tetrahydropyrimidine-2,6-dione.

9. The compound according to claim 1, which is 1-(7-chloro-2-ethyl-5-fluorobenzo[b]furan-4-yl)-3-methyl-4-trifluoromethyl-1,2,3,6-tetrahydropyrimidine-2,6-dione.

10. The compound according to claim 1, which is 3-amino-1-(7-chloro-2-ethyl-5-fluorobenzo[b]furan-4-yl)-4-trifluoromethyl-1,2,3,6-tetrahydropyrimidine-2,6-dione.

11. The compound according to claim 1, which is 3-amino-1-(5,7-difluoro-2-methylbenzo[b]furan-4-yl)-4-trifluoromethyl-1,2,3,6-tetrahydropyrimidine-2,6-dione.

12. The compound according to claim 1, which is 1-(7-chloro-5-fluoro-2-methylbenzo[b]furan-4-yl)-3-methyl-4-trifluoromethyl-1,2,3,6-tetrahydropyrimidine-2,6-dione.

13. A compound of the formula:

[Chemical structure with substituents A, Y, X, R', R'' on a benzofuran-type ring with NH$_2$ group]

wherein R' and R'' are, the same or different, each a hydrogen atom or a lower alkyl group, A is a hydrogen atom, a fluorine atom or a chlorine atom, X is an oxygen atom or a sulfur atom and Y is a hydrogen atom, a fluorine atom, a chlorine atom or a bromine atom.

14. The compound according to claim 13, wherein R' and R'' are both hydrogen atoms.

15. The compound according to claim 14, wherein Y is a chlorine atom and A is a fluorine atom, if X is a sulfur atom.

16. A herbicidal composition which comprises as an active ingredient a herbicidally effective amount of the compound according to claim 1, and an inert carrier or diluent.

17. A herbicidal composition which comprises as an active ingredient a herbicidally effective amount of the compound according to claim 2 and an inert carrier or diluent.

18. A herbicidal composition which comprises as an active ingredient a herbicidally effective amount of the compound according to claim 3 and an inert carrier or diluent.

19. A herbicidal composition which comprises as an active ingredient a herbicidally effective amount of the compound according to claim 4 and an inert carrier or diluent.

20. A method for exterminating undesired weeds, which comprises applying a herbicidally effective amount of the compound according to claim 1 and an inert carrier or diluent to the area where the undesired weeds grow or will grow.

21. A method for exterminating undesirable weeds, which comprises applying a herbicidally effective amount of the compound according to claim 2 and an inert carrier or diluent to the area where the undesired weeds grow or will grow.

22. A method for exterminating undesirable weeds, which comprises applying a herbicidally effective amount of the compound according to claim 3 and an inert carrier or diluent to the area where the undesired weeds grow or will grow.

23. A method for exterminating undesirable weeds, which comprises applying a herbicidally effective amount of the compound according to claim 4 and an inert carrier or diluent to the area where the undesired weeds grow or will grow.

* * * * *